(12) United States Patent
Cahalan et al.

(10) Patent No.: US 8,114,465 B2
(45) Date of Patent: Feb. 14, 2012

(54) PROCESS FOR PREPARING A SUBSTRATE COATED WITH A BIOMOLECULE

(75) Inventors: Patrick Cahalan, Cape Coral, FL (US); Linda Cahalan, Cape Coral, FL (US); Greg Johnson, Pittsburgh, PA (US); Mark Gartner, Wexford, PA (US)

(73) Assignee: Ension, Inc., Pittsburgh, PA (US)

( * ) Notice: Subject to any disclaimer, the term of this patent is extended or adjusted under 35 U.S.C. 154(b) by 987 days.

(21) Appl. No.: 12/061,212

(22) Filed: Apr. 2, 2008

(65) Prior Publication Data

US 2008/0241349 A1 Oct. 2, 2008

Related U.S. Application Data

(60) Provisional application No. 60/909,553, filed on Apr. 2, 2007.

(51) Int. Cl.
B05D 3/04 (2006.01)
(52) U.S. Cl. ........................ 427/2.13; 427/2.3
(58) Field of Classification Search .............. 427/2.13, 427/2.3
See application file for complete search history.

(56) References Cited

U.S. PATENT DOCUMENTS

| | | | |
|---|---|---|---|
| 3,905,823 A * | 9/1975 | Piskoti | 106/38.22 |
| 4,613,665 A | 9/1986 | Larm | |
| 4,975,247 A | 12/1990 | Badolato et al. | |
| 5,049,403 A | 9/1991 | Larm et al. | |
| 5,112,457 A | 5/1992 | Marchant | |
| 5,182,317 A | 1/1993 | Winters et al. | |
| 5,395,468 A | 3/1995 | Juliar et al. | |
| 5,811,151 A | 9/1998 | Hendriks et al. | |
| 6,024,918 A | 2/2000 | Hendriks et al. | |
| 6,270,788 B1 | 8/2001 | Koulik et al. | |
| 6,379,691 B1 | 4/2002 | Tedeschi et al. | |
| 6,436,481 B1 | 8/2002 | Chabrecek et al. | |
| 6,461,665 B1 | 10/2002 | Scholander | |
| 6,509,104 B2 | 1/2003 | Huang et al. | |
| 6,559,132 B1 | 5/2003 | Holmer | |
| 6,632,470 B2 | 10/2003 | Morra et al. | |
| 6,756,125 B2 | 6/2004 | Al-Lamee | |
| 6,830,583 B2 | 12/2004 | Shah et al. | |
| 6,921,811 B2 | 7/2005 | Zamora et al. | |
| 7,034,061 B1 | 4/2006 | Luthra et al. | |
| 7,129,224 B1 | 10/2006 | Byun et al. | |
| RE39,438 E | 12/2006 | Shah et al. | |
| 2006/0246291 A1 | 11/2006 | Kunz et al. | |

FOREIGN PATENT DOCUMENTS

WO 2005033219 5/2005
WO 2005082434 9/2005

* cited by examiner

*Primary Examiner* — Peter Szekely
(74) *Attorney, Agent, or Firm* — Blynn L. Shideler; Krisanne Shideler; BLK Law Group

(57) ABSTRACT

Processes are provided for preparing a substrate coated with a biomolecule, comprising:
  a) providing a substrate;
  b) coating the substrate with a polysiloxane, typically by exposing the substrate to a reactive gas containing siloxane functional groups and to plasma energy to yield a plasma-deposited polysiloxane surface on the substrate;
  c) rendering the polysiloxane surface amino functional; and
  d) contacting the amino-functional polysiloxane surface with a biomolecule under conditions effective to attach the biomolecule to the substrate.

The coated substrate may be a medical device that demonstrates an ability to maintain gas permeability when in contact with blood or blood components, compared to a substantially identical medical device that has not been coated with a biomolecule using this process.

20 Claims, No Drawings

PROCESS FOR PREPARING A SUBSTRATE COATED WITH A BIOMOLECULE

The present invention claims the benefit of provisional patent application Ser. No. 60/909,553 entitled "Process for Preparing a Substrate Coated with a Biomolecule" filed Apr. 2, 2007.

FIELD OF THE INVENTION

The present invention relates to processes for preparing substrates coated with biomolecules, in particular medical devices with surfaces coated with biomolecules, such as blood oxygenator fibers coated with heparin.

BACKGROUND OF THE INVENTION

Devices used in the medical field must be manufactured using materials, such as biomaterials, having particular surface properties so that the device functions without causing adverse effects to the patient.

Biomaterials are typically made of inert metals, polymers, or ceramics to ensure durability and to ensure that the materials do not adversely react with the physiological environment with which they come into contact, such as with blood or tissues. More particularly, many biomedical devices may or may not require blood compatible, infection resistant, and/or tissue compatible surfaces. For example, it is often desirable to manufacture medical devices, such as catheters, that have properties that discourage adherence of blood or tissue elements to the device.

It is also desirable for certain biomaterials, such as those for implants, to be anchored stably into the tissue environment into which they are implanted. For example, it may be desirable for specific implants, such as certain types of catheters and stents, to be non-inflammatory and anchored to the surrounding tissues. Moreover, it may be desirable for certain biomaterials to prevent bacterial growth during a course of a procedure, or as a permanent implant so as to prevent infection of a patient in contact with the biomaterial. Initial contact of such materials with blood may result in deposition of plasma proteins, such as albumin, fibrinogen, immunoglobulin, coagulation factors, and complement components. The adsorption of fibrinogen onto the surface of the material causes platelet adhesion, activation, and aggregation. Other cell adhesive proteins, such as fibronectin, vitronectin, and von Willebrand factor (vWF) also promote platelet adhesion.

In addition, disposable surgical tools may become infected with bacteria during a course of a long operation and reuse of the tool during the operation may promote bacterial infection in the patient. For certain tools used in particular applications, it may be desirable therefore to prevent any bacterial growth on the surfaces of these tools during the course of an operation.

Additionally for permanently implanted materials it would be desirable to prevent bacterial growth that would lead to a biomaterial or device centered infection. In the latter the only remedy is eventual removal of the implant.

Adverse reactions between materials and blood components are predominant factors limiting the use of synthetic materials that come into contact with physiological fluids.

A number of approaches have been suggested to improve the biocompatibility and blood compatibility of medical devices. One approach has been to modify the surface of the material to prevent undesirable protein adhesion by providing the material with a low polarity surface, a negatively charged surface, or a surface coated with biological materials, such as enzymes, endothelial cells, and proteins. Another approach has been to bind anticoagulants to the surface of biologically inert materials to impart antithrombogenic characteristics to the materials. Still another approach used in the art has been the copolymerization of various phospholipids which are used as coating materials for various substrates. Partial polymeric backbone coatings have also been used in a similar fashion. However, many of these methods can result in a leaching or "stripping off" of the coating.

In devices requiring the transfer of gases, for example, in blood oxygenators requiring the exchange of oxygen and carbon dioxide through a membrane or porous fiber, there are additional drawbacks. Often surfaces that have been rendered biocompatible by the coating of biomolecules attract phospholipids. Phospholipids that adhere to the surface coat the pores and wet the surface of the device, making it hydrophilic. Water adversely affects gas transfer, making the oxygenator significantly less effective.

There is a need in the art to develop processes for preparing substrates coated biomolecules that demonstrate biocompatibility and blood compatibility, while maintaining gas permeability.

SUMMARY OF THE INVENTION

In accordance with the present invention, processes are provided for preparing a substrate coated with a biomolecule. A typical process comprises:
   a) providing a substrate;
   b) coating the substrate with a polysiloxane;
   c) rendering the polysiloxane surface amino functional; and
   d) contacting the amino-functional polysiloxane surface with a biomolecule under conditions effective to attach the biomolecule to the substrate.

Note that the order of some of the process steps may be altered or steps may be combined and performed simultaneously with the same results and without departing from the scope of the invention. Also, additional steps such as cleaning steps may be added as necessary, discussed hereinafter.

DETAILED DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

All numerical ranges herein include all numerical values and ranges of all numerical values within the recited numerical ranges. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The various embodiments and examples of the present invention as presented herein are each understood to be non-limiting with respect to the scope of the invention.

As used in the following description and claims, the following terms have the indicated meanings:

The term "cure", "cured" or similar terms, as used in connection with a cured or curable composition, e.g., a "cured composition" of some specific description, means that at least a portion of the polymerizable and/or crosslinkable components that form the curable composition is at least partially polymerized and/or crosslinked. For example, the degree of crosslinking can range from 5% to 100% of complete crosslinking. In alternate embodiments, the degree of crosslinking can range from 35% to 85%, e.g., 50% to 85%, of full crosslinking. The degree of crosslinking can range between any combination of the previously stated values, inclusive of the recited values.

The term "curable", as used for example in connection with a curable film-forming composition (coating), means that the indicated composition is polymerizable or cross linkable, e.g., by means that include, but are not limited to, thermal, catalytic, electron beam, chemical free-radical initiation, and/or photoinitiation such as by exposure to ultraviolet light or other actinic radiation.

The terms "on", "appended to", "affixed to", "bonded to", "adhered to", or terms of like import means that the designated item, e.g., a coating, film or layer, is either directly connected to (superimposed on) the object surface, or indirectly connected to the object surface, e.g., through one or more other coatings, films or layers (superposed on).

The terms "attach", "couple", and "link" refer to securing a coating or biomolecule to a substrate, for example, by chemical covalent or ionic bonding, such that the coating or biomolecule is immobilized with respect to the substrate.

The term "rigid", as used for example in connection with a substrate, means that the specified item is self-supporting.

The phrase "an at least partial film" means an amount of film covering at least a portion, up to the complete surface of the substrate. As used herein, a "film" may be formed by a sheeting type of material or a coating type of material. For example, a film may be an at least partially cured polymeric sheet or an at least partially cured polymeric coating of the material indicated. The phrase "at least partially cured" means a material in which from some to all of the curable or cross-linkable components are cured, crosslinked and/or reacted.

The term "medical device" may be a device that has surfaces that contact tissue, blood, or other bodily fluids in the course of its operation, which fluids are subsequently introduced into patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like which are placed into the blood vessels or the heart for purposes of monitoring or repair.

The term "biomolecule" refers to a biologically active molecule.

A "biocompatible" material does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as infection, coagulation, tissue death, tumor formation, allergic reaction, foreign body reaction (rejection) or inflammatory reaction.

A "blood compatible" material is one that will not induce undesirable reactions in the body as a result of contact with blood, such as blood clotting or infection. A blood compatible material is understood to be biocompatible.

According to the present invention, processes are provided for preparing a substrate coated with a biomolecule. A typical process comprises:

a) providing a substrate;
b) coating the substrate with a polysiloxane;
c) rendering the polysiloxane surface amino functional; and
d) contacting the amino-functional polysiloxane surface with a biomolecule under conditions effective to attach the biomolecule to the substrate.

The surface of the resulting coated substrate is biocompatible and preferably blood compatible. In particular, the resulting coated substrate is permeable to oxygen and carbon dioxide and remains so during exposure to bodily fluids by preventing adhesion of phospholipids.

Substrates suitable for use in the process of the present invention include metals, polymers, ceramic and glass. They are substantially insoluble in body fluids and are generally designed and constructed to be placed in or onto the body or to contact fluid of the body, most often blood. The substrates have the physical properties such as strength, elasticity, permeability and flexibility required to function for their intended purpose, and are typically rigid, i.e., capable of maintaining their shape and supporting any subsequently-applied coatings or films. The substrates can be purified, fabricated and sterilized easily; will substantially maintain their physical properties and function during the time that they remain implanted in or in contact with the body or bodily fluid. Examples of such substrates include: metals such as titanium/titanium alloys, TiNi (shape memory/super elastic), aluminum oxide, platinum/platinum alloys, stainless steels, and other metal alloys known to be useful for medical devices, pyrolytic carbon, silver or glassy carbon; polymers such as polyurethanes, polycarbonates, silicone elastomers, polyolefins including polyethylenes or polypropylenes, polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, ethylene tetrafluoroethylene copolymer (ETFE), acrylonitrile butadiene ethylene, polyamide, polyimide, styrene acrylonitrile, and the like; minerals or ceramics such as hydroxapatite; human or animal protein or tissue such as bone, skin, teeth, collagen, laminin, elastin or fibrin; organic materials such as wood, cellulose, or compressed carbon; and other materials such as glass, or the like.

The substrate used in the process of the present invention often comprises a surface of a medical device. Substrates which may be coated with biomolecules in accordance with the present invention include, but are not limited to, those to be used in the manufacture of medical devices such as surgical implants, prostheses, and any artificial part or device which replaces or augments a part of a living body or comes into contact with bodily fluids, particularly blood. The substrates can be in any shape or form including tubular, sheet, rod and articles of shapes required for particular uses. Such shaped substrates are typically coated using the process of the present invention prior to manufacture of the medical device in which they are used. Various medical devices and equipment usable in accordance with the invention are known in the art. Examples of devices include catheters, suture material, tubing, and fiber membranes. Examples of catheters include central venous catheters, thoracic drain catheters, and angioplasty balloon catheters. Examples of tubing include tubing used in extracorporeal circuitry, such as whole blood oxygenators. Examples of membranes include polycarbonate membranes, haemodialysis membranes, and membranes used in diagnostic or biosensor devices. Also included are devices used in diagnosis, as well as polyester yarn suture material such as polyethylene ribbon, and polypropylene hollow fiber membranes. Further illustrations of medical devices include autotransfusion devices, blood filters, blood pumps, blood temperature monitors, bone growth stimulators, breathing circuit connectors, bulldog clamps, cannulae, grafts, implantible pumps, impotence and incontinence implants, intra-ocular lenses, leads, lead adapters, lead connectors, nasal buttons, orbital implants, cardiac insulation pads, cardiac jackets, clips, covers, dilators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, such as fabrics, felts, mesh, patches, cement spacers, cochlear implant, defibrillators, generators, orthopedic implants, pacemakers, patellar buttons, penile implants, pledgets, plugs, ports, prosthetic heart valves, sheeting, shunts, umbilical tape, valved conduits, and vascular access devices.

The method of the present invention also is particularly applicable to blood gas exchange devices, e.g., oxygenators. This includes both sheet and tubular forms of membrane oxygenators, which are well known in the art. In a membrane oxygenator, the blood is separated from direct contact with the oxygenating gas by a membrane, which is disposed within a hollow housing. This membrane is microporous or semipermeable, that is, capable of permitting carbon dioxide and oxygen to permeate through it while at the same time preventing the blood itself from passing therethrough.

There currently are two types of membrane oxygenators. One type is referred to as a hollow fiber oxygenator, and is illustrated in U.S. Pat. No. 4,239,729 (Hasegawa et al). A hollow fiber oxygenator employs a large plurality (typically thousands) of microporous or semipermeable hollow fibers disposed within a housing. These hollow fibers are sealed in the end walls of the housing; the end walls are then fitted with skirted end caps. One end cap is fitted with an inlet, and the other is fitted with an outlet. In the Hasegawa et al. oxygenator, the hollow fibers are aligned in the housing so that their longitudinal axes are generally parallel to the longitudinal axis of the housing. In this device, blood enters through the inlet of one end cap, passes through the lumens of the hollow fibers, and exits through the outlet of the other end cap. Oxygenated gas enters the device through the inlet in the peripheral wall near one end of the device, passes over the outer surfaces of the hollow fibers, and exits the device through the outlet in the peripheral wall near the other end of the device. It will be understood that carbon dioxide diffuses from the blood flowing inside the hollow fibers through the fiber walls into the stream of oxygenating gas. At the same time, oxygen from the oxygenating gas flowing over the outer surfaces of the hollow fibers diffuses through the walls of the hollow fibers into the lumens thereof to oxygenate the blood flowing therethrough.

Since the development of this type of oxygenator, other oxygenators comprising hollow fibers have been developed. These oxygenators typically comprise a plurality of hollow fibers disposed within a hollow housing and arranged so that blood typically flows over the hollow fibers and gases typically flow through the hollow fibers. Many configurations are possible as to the direction of fluid flow and the arrangement of fibers. The fibers may be in a linear, circular, or spiral arrangement, for example, or may be wrapped or wound around a core in various configurations. Hollow fiber membrane oxygenators are described, for example, in U.S. Pat. No. 4,975,247 (Badolato, et al) and U.S. Pat. No. 5,395,468 (Juliar, et al). In certain embodiments of the present invention, the substrate being coated comprises hollow fibers that are to be used in the manufacture of a blood oxygenator.

A second type of membrane oxygenator, called the flat plate membrane oxygenator, employs one or more thin, flat sheets of microporous membrane. In its most basic form, the flat plate oxygenator has a single sheet of microporous membrane sealed into a housing so as to provide in the housing a first compartment (the "blood compartment") for the flow of blood, and a second compartment (the "gas compartment") for the flow of an oxygenating gas. Each of the compartments is fitted with an inlet and an outlet. Blood flows into and out of the blood compartment and the oxygenating gas flows into and out of the gas compartment. Oxygen passes from the oxygenating gas across the membrane into the blood flowing through the blood compartment. Carbon dioxide passes from the entering blood across the membrane to be entrained in the oxygenating gas. The exiting blood, now reduced in carbon dioxide and enriched in oxygen, is returned to the patient.

In certain embodiments of the present invention, the process may include a step of cleaning the substrate prior to step b) of the process, to remove any surface contaminants or impurities. Such cleaning may be done, for example, by placing the substrate in a plasma chamber, infusing air, oxygen, and/or nitrogen into the plasma chamber, and then exposing the device to plasma energy. Air and oxygen plasma treatments introduce oxygen containing functionalities on the surface of polymeric substrates. For example, hydroxyl, carboxyl, and other oxygen containing functionalities are introduced on the surface of polyethylene. As a result, the surface becomes more polar and wettability increases. Low molecular weight contaminants are effectively removed by the combined effect of plasma and vacuum. Air plasma treatment of metallic substrate materials mostly provides a cleaning effect, removing hydrocarbons and other organic contaminants from the metal surface. Plasma treatment for cleaning purposes may be conducted in the same manner as reactive gas treatment, discussed below.

In step b) of the process of the present invention, the substrate is coated with a polysiloxane. This coating step may be accomplished in any of several manners. It is possible to contact the substrate with a polysiloxane in a liquid carrier. Contact may be by brushing, dipping (immersion), flow coating, spraying and the like. Immersion may include stirring or other agitation of the coating composition, by use of a stirring device or by movement of the substrate to be coated through the composition. More often, however, the substrate is exposed to a reactive gas containing siloxane functional groups and plasma energy to yield a plasma-deposited polysiloxane surface on the substrate. Such plasma treatments typically take place within a plasma chamber containing electrodes, across which a voltage is applied, as known in the art. A stream of gas is fed into the chamber. Gases may vary and include, for example, hexamethyldisiloxane and/or tetramethyldisiloxane. When a high frequency voltage is applied between the electrodes, current flows into the chamber, forming a plasma, which is a glowing electrical discharge within the gas. Reactive chemical species are formed in this electrical discharge.

The plasma-deposited surface comprises a polymeric layer deposited onto the substrate. Siloxane molecules are fragmented in the plasma phase and recombine to yield a high molecular weight polymeric compound that deposits as a film on the device surface. The structure of the deposited film depends on the stream gas chemistry and the treatment conditions. Films deposited by this plasma process are, typically, highly cross-linked, pin-hole free, homogeneous, and show good adhesion to the device. Following cessation of the high frequency voltage applied between the electrodes, the gas stream flow may be continued in the chamber in order to quench the substrate.

Step c) of the process of the present invention comprises rendering the polysiloxane surface amino functional. In certain embodiments of the present invention, step c) comprises contacting the polysiloxane surface with an amino- and/or imino-functional compound for a time sufficient to effect adsorption of the amino- and/or imino-functional compound onto the polysiloxane surface. In such embodiments, the amino- and/or imino-functional compound may comprise polyethyleneimine, an amino-functional silane and/or diaminopropane. Examples of suitable amino functional silanes include amino-functional silanes sold as the Dow Corning Z-silane series. Depending on the identity of the compound, it may be present in a liquid carrier, particularly when the compound is an amino-functional silane. Again, contact may be by brushing, dipping (immersion), flow coating, spraying and the like, but is typically by immersion. After adsorption of the compound onto the surface, any imino-functional groups may be reduced to amino-functional groups by addition of a suitable reducing agent to the liquid carrier.

Alternatively, step c) may comprise exposing the plasma-deposited polysiloxane surface to ammonia or an organic amino-functional gas and to plasma energy to yield an amino-functional plasma-deposited surface. Suitable organic amino-functional gases include amino-functional polysiloxane, diaminopropane, and allyl amine.

Prior to attachment of the biomolecule to the amino-functional polysiloxane surface in step d), it may be desirable to expose the amino-functional polysiloxane surface to a reactive gas containing acrylic acid and to plasma energy to yield a plasma-deposited polyacrylic acid coating on the surface. This step is particularly useful when the polysiloxane has been applied using plasma energy, and is suitable for the preparation of medical devices that do not facilitate mass transfer such as gas exchange.

In step d) of the process of the present invention, the amino-functional polysiloxane surface is contacted with a biomolecule under conditions effective to attach the biomolecule to the substrate. Examples of biomolecules that may be attached to the surface include antibacterial agents, antimicrobial agents, anticoagulants, antithrombotic agents, platelet agents, anti-inflammatories, enzymes, catalysts, hormones, growth factors, drugs, vitamins, antibodies, antigens, nucleic acids, dyes, a DNA segment, an RNA segment, protein, and peptides. Often, when the medical device to be coated is designed to come in contact with blood, in particular when the medical device is a blood oxygenator, the biomolecule comprises heparin.

Attachment of the biomolecule to the amino-functional polysiloxane surface can be accomplished by any of a number of methods known to those skilled in the art. One particularly preferred method is an oxidation method involving the use of periodate. The biomolecule, usually heparin, is contacted with a periodate in a buffered aqueous solution and allowed to react. This controlled oxidation provides a limited number of reactive aldehyde groups per molecule. The periodate is a water-soluble periodate, preferably, an alkali metal periodate, such as sodium periodate. When the biomolecule is heparin, the amount of periodate used is sufficient to react with no more than two of the sugar units in the heparin molecule (i.e., the basic disaccharide residues constituting the structure of the glycosaminoglycan). If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to about 8 can be used. A lower pH (e.g., an acetate buffer at pH 4.5) is preferred if a rapid reaction is desired while a more neutral pH (e.g., a phosphate buffer at pH 6.88) is preferred for a slower reaction with a longer storage life. With the acetate buffer at a pH of 4.5, the reaction should proceed for about 3 hours, while with a phosphate buffer at a pH or 6.88, the reaction should proceed for about 16 hours. If desired, the reacted mixture may then be stored prior to use at about 5° C.

The reacted mixture is diluted and the pH adjusted in order to bring the pH of the mixture to a pH that is favorable for the coupling reaction between the biomolecule and the amino-functional polysiloxane. A mild reducing agent, such as sodium cyanoborohydride, is added to the diluted mixture to effect the reduction of the bonds formed between the reactive aldehyde groups on the oxidized biomolecule and the amine functional groups on the polysiloxane coated on the substrate surface. The substrate surface being treated is then contacted with (e.g., immersed in or flushed with) the diluted mixture at a sufficient temperature and for a sufficient time to complete the reaction (i.e., attach the biomolecule). This time can range from about 30 seconds to about 2 hours at temperatures ranging from about 20° C. to about 60° C. For example, at room temperature (i.e., about 20° C. to about 25° C.), the substrate coated with the amino-functional polydimethylsiloxane can be flushed with a solution of a biomolecule over a period of 30 seconds to 5 minutes for effective biomolecule attachment.

Substrates coated with biomolecules according to the process of the present invention are biocompatible, and are typically blood compatible, while remaining permeable to gases including oxygen and carbon dioxide.

The present invention is more particularly described in the following examples, which are intended to be illustrative only, since numerous modifications and variations therein will be apparent to those skilled in the art. Unless otherwise specified, all parts and percentages are by weight.

EXAMPLES

One group of modified bulk material was prepared, a total of 34 hollow fiber strips underwent a 40 sec $O_2/N_2$ plasma cleaning followed by a 40-second siloxane deposition. Within 48 to 72 hours the siloxane treated material was heparinized. (NH)

Materials and Methods
1. Microporous Hollow Fiber Membrane Bulk Material Lot# 13502-4-4 precut to 36" lengths
2. Glass microscope slide
3. Siloxane-Tetramethyldisiloxane, 97% P/N 235733// Batch 04526KC (Aldrich)
4. For chemical list see table IV Set-Up and Pre-Testing
1. Glass microscope slide
2. After placing the glass slide in the reactor and pulling vacuum to <100 mtorr, oxygen was allowed through the mass flow controller (MFC1) at a rate of 20% and $N_2$ through MFC2 at a rate of 80% of total flow, and the pressure control was set to 250 motor. Plasma power was set for 200 W (power). See table I below Pre-Test for Uniformity of Siloxane Deposition on Glass Slide

TABLE I

| Material Description | Process Description | Pressure (mtorr) | MFC1/MFC2 | Set Power Watts | Time Seconds | Siloxane Temperature Set Point | Comments |
|---|---|---|---|---|---|---|---|
| Glass microscope slide and PP HF | 20% $O_2$ 80% $N_2$ Clean | 250 | 0.2/.8 | 200 | 40 | NA | Contact angle 0 - wet out |
| | Siloxane Deposition | 250 | NA | 200 | 40 | NA | Contact angle >90 - non wet |

Set-Up Procedure

Siloxane vapors from a feed chamber were introduced through a ball valve that communicated with the plasma reactor. Vacuum was pulled to <100 mtorr before opening the ball valve. The valve was opened to control pressure at 250 mtorr from the siloxane vapor.

Results from first test for uniform coverage in the reactor showed that the glass slide made the conversion from hydrophilic to hydrophobic.

Siloxane Deposition of Bulk Material
1. Two 36" hollow fiber strips per/run were placed on the reactor tray and carefully taped underneath. See diagram below
2. $O_2//N_2$ cleaned for 40 seconds
3. Siloxane deposition 40 seconds
4. Contact angle was performed on a glass microscope slide after each siloxane treatment/run.
5. For storage and transporting after siloxane deposition, the strips were placed between lint-free towels.

TABLE II

| Material Description | Process Description | Run Number | Pressure (mtorr) | MFC1/MFC2 | Set Power Watts | Time Seconds | Siloxane Temperature Set Point | Contact Angle Glass Slide |
|---|---|---|---|---|---|---|---|---|
| (2) 36 × 4" Strips | $O_2//N_2$ Clean | 1 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 2 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 3 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 4 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 5 | 250 | 0.2 | 200 | 40 | NA | 0 - wet out |

TABLE II-continued

| Material Description | Process Description | Run Number | Pressure (mtorr) | MFC1/ MFC2 | Set Power Watts | Time Seconds | Siloxane Temperature Set Point | Contact Angle Glass Slide |
|---|---|---|---|---|---|---|---|---|
| (1) Glass Slide | Siloxane | | | 0.8 | | 40 | | >90 - non wet |
| (2) 36 × 4" Strips | $O_2//N_2$ Clean | 6 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 7 | 250 | 0.2 | 200 | 40 | NA | 0 - wet out |
| (1) Glass Slide | Siloxane | | | 0.8 | | 40 | | >90 - non wet |
| (2) 36 × 4" Strips | $O_2//N_2$ Clean | 8 | 250 | 0.2 | 200 | 40 | NA | 0 - wet out |
| (1) Glass Slide | Siloxane | | | 0.8 | | 40 | | >90 - non wet |

Wet Chemistries (PEI and Heparin)

34 siloxane treated bulk material sheets (pre-cut to ~17× 4") then carefully layered into (2) vessels and modified as follows.
Step One—Polyethyleneimine (PEI) Amination:
Preparation of BASF PEI solution [0.1%]: Total=1800 g
1764 g 0.1M Borate Buffer pH 9.0
36 ml of a 5% BASF PEI stock solution PEI and borate buffer were combined a glass beaker and allowed to stir for 15 minutes, the PEI solution was dispensed into (2) 2000 ml rectangle vessels each containing 16 (17×4") layered material strips. The container's were covered and placed on an orbital shaker and allowed to agitate @90 rpm for 75 minutes @ ambient temperature. After PEI adsorption, the aminated material was rinsed several times with DI $H_2O$. After rinsing a small sample was removed, stained with Ponceau S and evaluated for uniformity.
Ponceau S Staining Results:

The aminated sample showed a light uniform pink stain, indicating uniform coverage of PEI.
Step Two—Heparinization:
Preparation of Deaminated Heparin (DH) solution Total=1800 g

| 1.8 g | DH heparin = [1 mg/ml] |
| 1800 g | 0.5M NaCl adjust to pH 4.0 |
| 0.18 g | $NaCNBH_3$ = [0.1 mg/ml] |

Heparin was dissolved in the pre-mixed NaCl solution, then adjusted to pH 4.0±0.1, the solution was then preheated to 55° C. After the solution reached temperature the NaBHCN$_3$ was added and allowed to mix for 5-10 minutes. The preheated heparin solution was dispensed into (2) 2000 ml rectangle vessel containing the aminated material, the container's were covered and placed in a pre-heated 55° C. Orbital shaker @90 rpm for 2 hours 55° C. After heparinization the modified material was rinsed with DI $H_2O$, 1M NaCl, followed with a final DI rinse. After rinsing a small section was removed, stained with Toluidine Blue and evaluated for uniformity.
Toluidine Blue O Staining Results:

Visual observations showed the heparinized sample to have a light but uniform purple stain, indicating uniform coverage of heparin.

Whereas particular embodiments of this invention have been described above for purposes of illustration, it will be evident to those skilled in the art that numerous variations of the details of the present invention may be made without departing from the invention as defined in the appended claims and equivalents thereto.

What is claimed is:

1. A process for preparing a substrate coated with a biomolecule comprising:
 a) providing a substrate;
 b) coating the substrate with a polysiloxane by exposing the substrate to a reactive gas containing siloxane functional groups and to plasma energy to yield a plasma-deposited polysiloxane surface on the substrate;
 c) rendering the polysiloxane surface amino functional after the step of coating the substrate with a polysiloxane; and
 d) contacting the amino-functional polysiloxane surface with a biomolecule under conditions effective to attach the biomolecule to the substrate by a reaction between the biomolecule and the amino-functional polysiloxane.

2. The process of claim 1 wherein the substrate is a metal, polymer, ceramic, or glass.

3. The process of claim 2 wherein the substrate is a surface of an article to be used in the manufacture of a medical device.

4. The process of claim 3 wherein the medical device is a blood oxygenator.

5. The method of claim 4 wherein the medical device is a blood oxygenator and the substrate being coated comprises hollow fibers.

6. The process of claim 1 wherein the reactive gas containing siloxane functional groups is selected from the group consisting of hexamethyldisiloxane and tetramethyldisiloxane.

7. The process of claim 1 wherein step c) comprises contacting the polysiloxane surface with an amino- and/or imino-functional compound for a time sufficient to effect adsorption of the amino- and/or imino-functional compound onto the polysiloxane surface.

8. The process of claim 7 wherein the amino- and/or imino-functional compound comprises polyethyleneimine, an amino-functional silane and/or diaminopropane.

9. The process of claim 1 wherein step c) comprises exposing the plasma-deposited polysiloxane surface to ammonia or an organic amino-functional gas and to plasma energy to yield an amino-functional plasma-deposited surface.

10. The process of claim 9 wherein the plasma-deposited polysiloxane surface is exposed to an organic amino-functional gas selected from amino-functional polysiloxane, diaminopropane, and allyl amine.

11. The process of claim 1 wherein step d) comprises contacting the amino-functional polysiloxane surface with a biomolecule in a liquid carrier at a temperature of at least 20° C. for at least 30 seconds.

12. The process of claim 11 wherein the liquid carrier further comprises a periodate in a buffered aqueous solution.

13. The process of claim 12 wherein the periodate comprises an alkali metal periodate.

14. The process of claim 12 wherein the biomolecule comprises heparin and the periodate is present in a sufficient amount to form aldehyde groups on the heparin.

15. The process of claim 12 wherein the buffered aqueous solution has a pH in a range of about 4.5 to about 8.

16. The process of claim 1 wherein the biomolecule is selected from the group consisting of an antibacterial agent, an antimicrobial agent, an anticoagulant, an antithrombotic agent, a platelet agent, an anti-inflammatory compound, an enzyme, a catalyst, a hormone, a growth factor, a drug, a vitamin, an antibody, an antigen, a nucleic acid, a dye, a DNA segment, an RNA segment, a protein, and a peptide.

17. The process of claim 1, further comprising, prior to step b), a step of placing the substrate in a plasma chamber, infusing air, oxygen, and/or nitrogen into the plasma chamber, and then exposing the device to plasma energy to clean the substrate surface.

18. The process of claim 1 wherein the surface formed is biocompatible.

19. The process of claim 18 wherein the surface formed is blood compatible.

20. A process for preparing a substrate coated with a biomolecule comprising:
   a) providing a substrate;
   b) coating the substrate with a polysiloxane;
   c) rendering the polysiloxane surface amino functional after coating the substrate with a polysiloxane in step b); and
   d) contacting the amino-functional polysiloxane surface with a biomolecule under conditions effective to attach the biomolecule to the substrate by a reaction between the biomolecule and the amino-functional polysiloxane.

* * * * *